(12) United States Patent
Anglada et al.

(10) Patent No.: US 9,283,105 B2
(45) Date of Patent: Mar. 15, 2016

(54) LUMBAR SUPPORT BELT

(75) Inventors: Gérard Anglada, Saint Etienne (FR); Thomas Beckers, Gardabaer (IS)

(73) Assignee: GIBAUD, Saint Etienne (FR)

( * ) Notice: Subject to any disclaimer, the term of this patent is extended or adjusted under 35 U.S.C. 154(b) by 452 days.

(21) Appl. No.: 13/510,756

(22) PCT Filed: Jun. 21, 2010

(86) PCT No.: PCT/FR2010/051243
§ 371 (c)(1),
(2), (4) Date: Sep. 27, 2012

(87) PCT Pub. No.: WO2011/064476
PCT Pub. Date: Jun. 3, 2011

(65) Prior Publication Data
US 2013/0030337 A1    Jan. 31, 2013

(30) Foreign Application Priority Data

Nov. 25, 2009 (FR) ..................................... 09 58380

(51) Int. Cl.
*A61F 5/00* (2006.01)
*A61F 5/02* (2006.01)
*A61F 5/30* (2006.01)

(52) U.S. Cl.
CPC .. *A61F 5/028* (2013.01); *A61F 5/30* (2013.01)

(58) Field of Classification Search
USPC ........ 602/5, 19; 128/96.1, 99.1, 101.1; 2/311, 2/312; D24/190–192
See application file for complete search history.

(56) References Cited

U.S. PATENT DOCUMENTS

| | | |
|---|---|---|
| 232,420 A | 9/1880 | Smith |
| 321,145 A | 6/1885 | Spencer |
| 321,146 A | 6/1885 | Spencer |
| 386,642 A | 7/1888 | Mann |
| 571,749 A | 11/1896 | Colton |
| 601,446 A | 3/1898 | Mestler |
| 629,900 A | 8/1899 | Fosburgh |
| 772,926 A | 10/1904 | Colton |
| 787,894 A | 4/1905 | Colton |
| 1,393,188 A | 10/1921 | Whiteman |

(Continued)

FOREIGN PATENT DOCUMENTS

DE    1 197 192    7/1965
DE    EP 0027602 A2 *  4/1981  .............. A61F 5/028

(Continued)

OTHER PUBLICATIONS

International Search Report issued in PCT/FR2010/051243, Aug. 6, 2010.

*Primary Examiner* — Kim M Lewis
(74) *Attorney, Agent, or Firm* — Workman Nydegger

(57) ABSTRACT

A belt comprising an elastic band having a central portion and two end portions, wherein a cushion is fastened on the inner surface of the central portion of the band, centered relative to the transverse median axis. The cushion is in the shape of a V whereby the tip is oriented downward when the belt is worn, and has two flanges connected by a joining area. The cushion is designed and positioned so that, when the belt is worn, the free end portion of each flange bears on the corresponding iliac crest of the person, and the joining area is in contact with the area comprising the upper portion of the sacrum and the lower portion of the lumbar vertebrae.

9 Claims, 3 Drawing Sheets

(56) References Cited

U.S. PATENT DOCUMENTS

| | | | |
|---|---|---|---|
| 1,589,670 A * | 6/1926 | Vartia | 602/36 |
| 1,921,851 A * | 8/1933 | White | A41F 11/14 2/315 |
| 2,036,484 A | 4/1936 | Le May | |
| 2,100,964 A | 11/1937 | Kendrick | |
| 2,219,475 A | 10/1940 | Flaherty | |
| 2,543,095 A * | 2/1951 | Davis | A61F 5/028 128/106.1 |
| 2,778,358 A * | 1/1957 | Keles | A61F 5/028 602/16 |
| 2,793,368 A | 5/1957 | Nouel | |
| 3,220,407 A * | 11/1965 | Connelly | 602/19 |
| 3,570,480 A | 3/1971 | Stubbs | |
| 3,920,008 A | 11/1975 | Lehman | |
| 3,927,665 A | 12/1975 | Wax | |
| 3,945,376 A | 3/1976 | Kuehnegger | |
| 4,384,372 A * | 5/1983 | Rector | 2/300 |
| 4,508,110 A | 4/1985 | Modglin | |
| 4,559,933 A | 12/1985 | Batard et al. | |
| 4,622,957 A | 11/1986 | Curlee | |
| 4,627,109 A * | 12/1986 | Carabelli et al. | 2/44 |
| 4,677,699 A | 7/1987 | Barabe | |
| 4,703,750 A * | 11/1987 | Sebastian et al. | 602/13 |
| 4,836,194 A * | 6/1989 | Sebastian | A61F 5/028 128/DIG. 20 |
| 5,060,639 A * | 10/1991 | Marcus | 602/19 |
| 5,188,585 A * | 2/1993 | Peters | 602/19 |
| 5,207,636 A * | 5/1993 | Striano | A61F 5/028 2/44 |
| 5,399,151 A | 3/1995 | Smith | |
| 5,421,809 A | 6/1995 | Rise | |
| 5,484,395 A | 1/1996 | DeRoche | |
| 5,528,771 A * | 6/1996 | Yudin | 602/19 |
| 5,599,287 A | 2/1997 | Beczak, Sr. et al. | |
| 5,690,609 A | 11/1997 | Heinze, III | |
| 5,707,364 A * | 1/1998 | Coates | 604/391 |
| 5,728,055 A * | 3/1998 | Sebastian | 602/19 |
| RE35,940 E | 10/1998 | Heinz et al. | |
| 5,984,885 A * | 11/1999 | Gaylord et al. | 602/19 |
| 6,099,490 A | 8/2000 | Turtzo | |
| 6,190,343 B1 | 2/2001 | Heinz et al. | |
| 6,213,968 B1 | 4/2001 | Heinz et al. | |
| 6,322,529 B1 | 11/2001 | Chung | |
| 6,419,652 B1 | 7/2002 | Slautterback | |
| 6,517,502 B2 | 2/2003 | Heyman et al. | |
| 6,602,214 B2 | 8/2003 | Heinz et al. | |
| 6,609,642 B2 | 8/2003 | Heinz et al. | |
| 6,676,620 B2 | 1/2004 | Schwenn et al. | |
| 6,702,770 B2 | 3/2004 | Bremer et al. | |
| 6,926,685 B1 | 8/2005 | Modglin | |
| 7,001,348 B2 | 2/2006 | Garth et al. | |
| 7,083,585 B2 | 8/2006 | Latham | |
| 7,101,348 B2 | 9/2006 | Garth et al. | |
| 7,118,543 B2 | 10/2006 | Telles et al. | |
| 7,186,229 B2 | 3/2007 | Schwenn et al. | |
| 7,201,727 B2 | 4/2007 | Schwenn et al. | |
| 7,306,571 B2 | 12/2007 | Schwenn et al. | |
| 7,316,660 B1 | 1/2008 | Modglin | |
| 7,320,670 B1 | 1/2008 | Modglin | |
| 7,329,231 B2 | 2/2008 | Frank | |
| 7,473,235 B2 | 1/2009 | Schwenn et al. | |
| 7,815,585 B2 | 10/2010 | Vollbrecht | |
| 2003/0220594 A1 | 11/2003 | Halvorson et al. | |
| 2004/0118412 A1 * | 6/2004 | Piletti-Reyes | A61F 5/30 128/876 |
| 2004/0133138 A1 | 7/2004 | Modglin | |
| 2005/0054960 A1 | 3/2005 | Telles et al. | |
| 2005/0059917 A1 | 3/2005 | Garth et al. | |
| 2005/0251074 A1 | 11/2005 | Latham | |
| 2005/0267390 A1 | 12/2005 | Garth et al. | |
| 2006/0052733 A1 | 3/2006 | Schwenn et al. | |
| 2006/0079821 A1 | 4/2006 | Rauch | |
| 2007/0179417 A1 | 8/2007 | Schwenn et al. | |
| 2007/0185425 A1 | 8/2007 | Einarsson et al. | |
| 2008/0045872 A1 * | 2/2008 | Bauerfeind et al. | 602/19 |
| 2008/0164293 A1 * | 7/2008 | Foissac et al. | 224/633 |
| 2008/0208091 A1 | 8/2008 | Vollbrecht et al. | |
| 2009/0192425 A1 | 7/2009 | Garth et al. | |
| 2009/0292230 A1 * | 11/2009 | Anquetil | A61F 5/028 602/19 |
| 2010/0217167 A1 | 8/2010 | Ingimundarson et al. | |
| 2010/0268141 A1 | 10/2010 | Bannister | |
| 2011/0112453 A1 * | 5/2011 | Petiot | A61F 5/028 602/19 |

FOREIGN PATENT DOCUMENTS

| | | | | |
|---|---|---|---|---|
| DE | 202 04 747 | | 7/2002 | |
| DE | 20 2004 015 328 | | 2/2005 | |
| DE | EP 1688107 A1 * | | 8/2006 | A61F 5/028 |
| FR | 1 104 562 | | 11/1955 | |
| FR | EP 0077760 A2 * | | 4/1983 | A61F 5/028 |
| FR | 2682869 A1 * | | 4/1993 | |
| FR | 2 952 807 | | 5/2011 | |
| FR | 2952807 A1 * | | 5/2011 | A61F 5/028 |
| GB | 909 970 | | 11/1962 | |
| GB | 2482309 A * | | 2/2012 | A61F 5/028 |
| GB | 2482309 A1 * | | 3/2012 | |
| JP | EP 2789316 A2 * | | 10/2014 | A61F 5/024 |
| NL | 1004821 C2 * | | 6/1998 | A61F 5/028 |
| WO | 03/017893 A1 | | 3/2003 | |
| WO | 2009/113053 A1 | | 9/2009 | |

* cited by examiner

LUMBAR SUPPORT BELT

CROSS REFERENCE TO RELATED APPLICATIONS

This application is the national stage of PCT/FR2010/051243, filed Jun. 21, 2010, which claims priority to French application No. FR0958380, filed Nov. 25, 2009, the entire contents of both of which are incorporated by reference in their entirety.

BACKGROUND

The present invention relates to a lumbar support belt.

Such a belt is intended for people suffering from lumbar pain, in particular, and traditionally comprises an elastic textile band intended to be positioned around the lower portion of a person's torso. This band has a central portion as well as first and second end portions provided with complementary fastening means and intended to be placed on one another opposite the person's abdominal region and to be assembled using said fastening means.

Thus positioned, the belt makes it possible on the one hand to decrease the pain felt by the wearer and on the other hand to keep the wearer in a good position, in particular owing to the splinting of the lumbar region and the abdominal region of the wearer.

In practice, it has been observed that the belt creates a significant load on the lower vertebrae, i.e. in particular the fourth and fifth lumbar vertebrae (L4-L5). This, aside from the pain felt by the wearer, is not fully satisfactory from an orthopedic perspective.

Furthermore, when the belt is tightened around the lower portion of a person's torso, the band, being stretched, cannot fit the shape of the lumbar curve and, as a result, cannot exert effective support in that area. However, it is primarily that area of the column that requires significant support.

The known orthopedic devices making it possible to resolve the aforementioned problems assume the form of relatively rigid corsets, made on a customized basis, and provided with stiffening means such as bones adapted to the patient's morphology. These devices are therefore expensive and generally heavy and uncomfortable.

There is therefore a need for a lumbar support with improved effectiveness and wearing comfort, and that can resolve the aforementioned drawbacks.

SUMMARY

In this context, the invention relates to a lumbar support belt comprising:
- an elastic textile band intended to be positioned around the lower portion of a person's torso, said band having a transverse median axis and having a central portion as well as first and second end portions which, provided with complementary attachment means, are intended to be placed on one another opposite the person's abdominal region and to be assembled by said attachment means; and
- a cushion fastened on the inner surface of the central portion of the band, substantially centered relative to the transverse median axis of the band.

According to a general definition of the invention, the cushion is substantially in the shape of a V whereof the tip is oriented downward when the belt is worn and having two flanges connected by a joining area, the cushion being designed and positioned so that, when the belt is worn, the free end portion of each flange bears on the corresponding iliac crest of the person and the joining area is in contact with the area comprising the upper portion of the sacrum and the lower portion of the lumbar vertebrae of the person.

By creating bearing on the iliac crests, i.e. by offsetting the bearing from the lumbar area toward the iliac crests, the belt makes it possible to decrease the mechanical pressure exerted by the top of the body on the lower vertebrae. By unloading the lower vertebrae in this way, by bearing on the so-called soft areas, a sort of elongation of the vertebral column is created that is very beneficial in terms of splinting. The flanges of the cushion also constitute a reference for the person wearing the belt, since by placing these flanges on the hips, the person ensures the proper positioning of the belt.

Furthermore, by providing, owing to the joining area of the cushion, contact substantially at the top of the gluteal fold, in the area of the fifth lumbar vertebra and the top of the sacrum (L5-S1), the belt ensures bearing in one of the most fragile areas of the column.

The belt according to the invention makes it possible to combine the effect of two bearings and substantially create a bearing continuity, especially for a person with pronounced lordosis. As a result, the mechanical effectiveness of the belt is greatly increased, without it being necessary to that end to tighten the band significantly. The wearing comfort is therefore improved.

Furthermore, the cushion, and more particularly the joining area of the cushion, contributes to filling in the empty area located in the lumbar curve. This makes it possible to improve the contact between the band and the wearer in that area and therefore the support imparted by the belt. This filling in being obtained by the cushion, which is a flexible element, and not by shaped rigid elements, such as bones, the belt can keep its advantages in terms of contact and support irrespective of the position of the wearer. The cushion therefore makes it possible to suitably adapt the belt to the anatomy of the person while guaranteeing the breathability of the belt through a suitable choice of the material used.

In order to improve the filling in of the wearer's lordosis, it is also possible to provide that the cushion includes an appendage extending from the joining area upward, when the belt is worn, substantially along the transverse median axis of the band.

Preferably, the area situated between the flanges of the cushion—whether the appendage is present or not—is not completely filled in.

According to one possible embodiment, shown in cross-section in a plane orthogonal to the band and passing through the transverse median axis, the appendage has a domed shape arranged to at least partially fill in the lordosis of the person wearing the belt.

The flanges of the cushion can be curved toward the inside of the V, to better adapt to the morphology of the wearer, in particular the hips.

When the belt is worn by a person, the free end of the flanges of the cushion is for example situated near each of the person's sides. Alternatively, the free end of the flanges of the cushion is situated in the lateral region of the person's abdomen.

Advantageously, the cushion can be removably attached to the band. In this way, it is possible to detach the cushion to wash it, or if the person wishes to wear the band alone, without the cushion. To that end, the cushion can comprise three attachment areas situated at the free end of the flanges and in the joining area, the inner surface of the band comprising three additional localized attachment areas. These may be gripping means such as loops and hooks in a Velcro® system.

By providing a cushion in a single piece provided with localized catching areas, the correct placement of the cushion on the band is facilitated, without possible interpretation by the wearer.

Alternatively, it is possible to provide for removable attachment of the cushion on the band, typically by sewing.

Furthermore, the belt can comprise at least one additional tightening strap. This feature is particularly advantageous in combination with the cushion according to the invention. In fact, these belts exist in a limited number of sizes. Depending on whether the wearer is at the upper or lower end of the anatomical range covered by the size of his belt, he may not obtain exactly the desired splinting with the band alone. The additional tightening strap(s) make it possible to better adjust the tightening and therefore improve the bearing obtained with the cushion, which translates favorably to the effectiveness of the belt.

BRIEF DESCRIPTION OF THE DRAWINGS

We will now describe, as non-limiting examples, several possible embodiments of the invention, in reference to the appended figures.

DETAILED DESCRIPTION OF PREFERRED EMBODIMENTS

Figure 1:
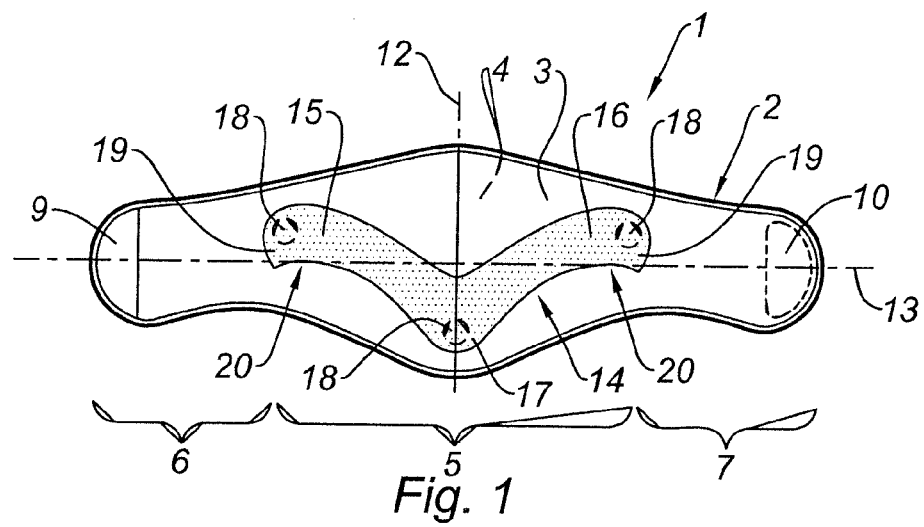
FIG. 1 is a planar view of the inner surface of a belt according to a first embodiment of the invention.

The belt 1 according to the invention comprises a band 2 that is made from an elastic textile and has an inner surface 3—turned toward the body of the wearer when the band is in the in-use position—and an outer surface 4.

The band 2 comprises a central portion 5 extended by first and second symmetrical end portions 6, 7. The central portion 5, which is widened relative to the end portions 6, 7, is intended to cover the lumbar region of the wearer. It can have bones (not shown) on its outer surface 4. For example, these bones are distributed into two groups of two parallel bones, and form a V converging downwardly and toward the transverse median axis of the band 2. The bones can be housed in gussets and have a concave curve housed in the concavity of the lumbar region of the wearer.

The band 2 is intended to be wound around the lower portion of a person's torso, the end portions 6, 7 being placed opposite one another on the person's abdominal region. In order to keep the band in that position, the first end portion 6 comprises, on its inner surface 3, an area 9 for gripping attachment means of the hook type of a Velcro® system and the second end portion 7 comprises, on its outer surface 3, a complementary area 10, for example an area of the type with loops of a Velcro® system. The attachment of the band 2 is then done by placing the first end portion 6 on the second end portion 7. However, the opposite structure is also possible.

The band 2 has a transverse median axis 12—substantially vertical when the belt 1 is worn—and a longitudinal median axis 13, substantially orthogonal to the transverse median axis and situated substantially at mid-height relative to the central portion 5.

The belt 1 also comprises a cushion 14 fastened on the inner surface 4 of the central portion 5 of the band 2, substantially centered relative to the transverse median axis 12 of the band 2. The cushion 14 is made from a flexible material allowing it to fit the shape of the person's body, and preferably a breathable material.

According to a first embodiment, illustrated in FIGS. 1 to 4, the cushion 14 is substantially in the shape of a flared V whereof the tip is oriented downward—when the belt 1 is worn. The cushion 14 has two flanges 15, 16 with a curved shape connected by a joining area 17, at the tip of the V. The angle formed between the flanges 15, 16 is for example comprised between 100° and 150°, in particular in the vicinity of 120°.

In the illustrated embodiment, the cushion 14 is fastened to the band 2 removably. To that end, the cushion 14 has, on its surface turned toward the band 2, three attachment areas 18 situated at the free end 19 of the flanges and in the joining area 17, while the band 2 has, on its inner surface 4, three additional localized attachment areas.

The attachment areas of the band 2 are formed so that, when the cushion 14 is fastened on the band 2 and the belt 1 is worn by a person in the appropriate position:

on the one hand, the free end portion 20 of each flange 15, 16 bears on the corresponding iliac crest 21 of the person;

and on the other hand, the joining area 17 is in contact with the area of the fifth lumbar vertebra (L5) and the top of the sacrum S (S1) of the person.

Figure 4:
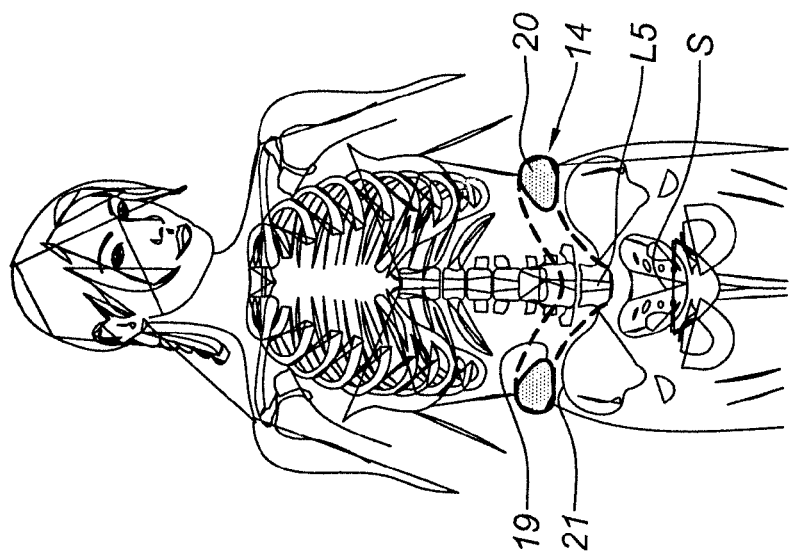
FIGS. 2 to 4 diagrammatically illustrate the belt of FIG. 1 placed on a person respectively seen from the back, side and front.
Figure 3:
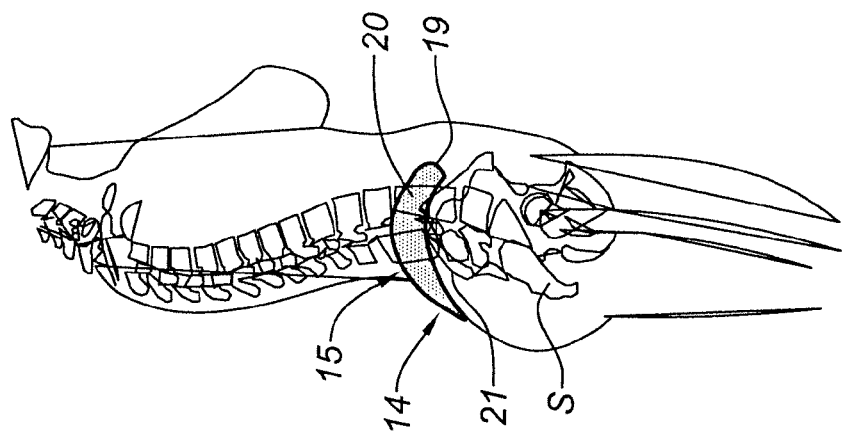
Figure 2:
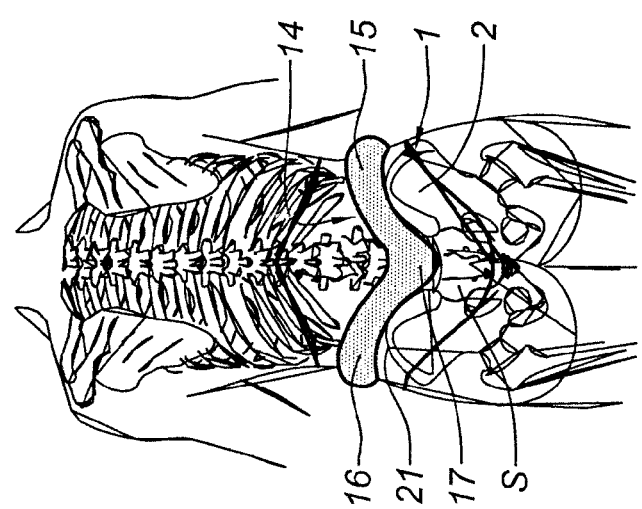
Figure 8:
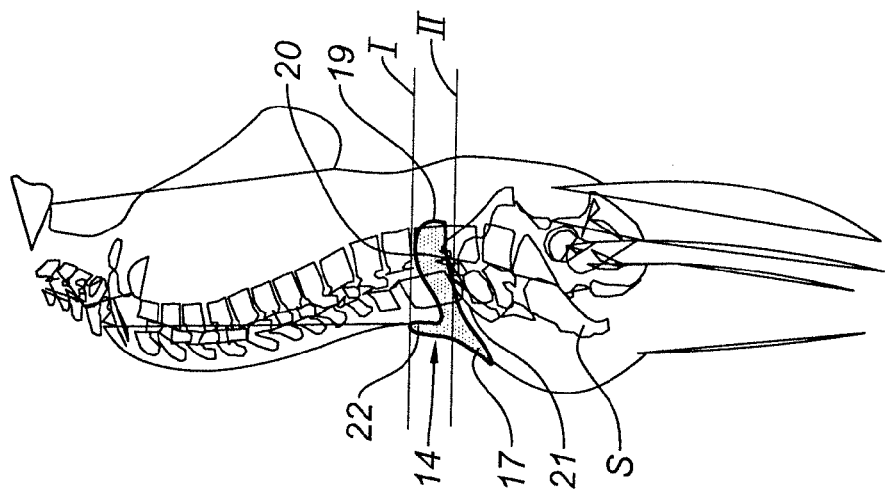
FIGS. 7 and 8 diagrammatically illustrate the belt of FIG. 5 placed on a person respectively seen from behind and the side.
Figure 7:
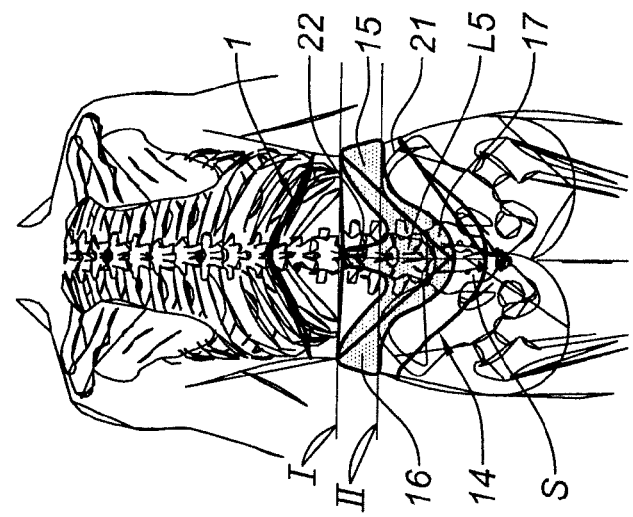

Furthermore, as shown in FIG. 4, the free end 19 of the flanges 15, 16 of the cushion 14 is situated in the lateral region of the person's abdomen.

The belt 1 can also comprise an additional tightening device (not shown).

According to a second embodiment, illustrated in FIGS. 5 to 10, the cushion 14 has substantially the same shape as previously described and also has an appendage 22. The appendage 22 extends from the joining area 17 upward, when the belt 1 is worn, substantially along the transverse median axis 12 of the band 2. Preferably, the appendage 22 has a domed shape seen in cross-section in a plane orthogonal to the band 2 and passing through the transverse median axis 12. In this way, better filling in of the lumbar curve of the person wearing the belt 1 is obtained.

Figure 5:
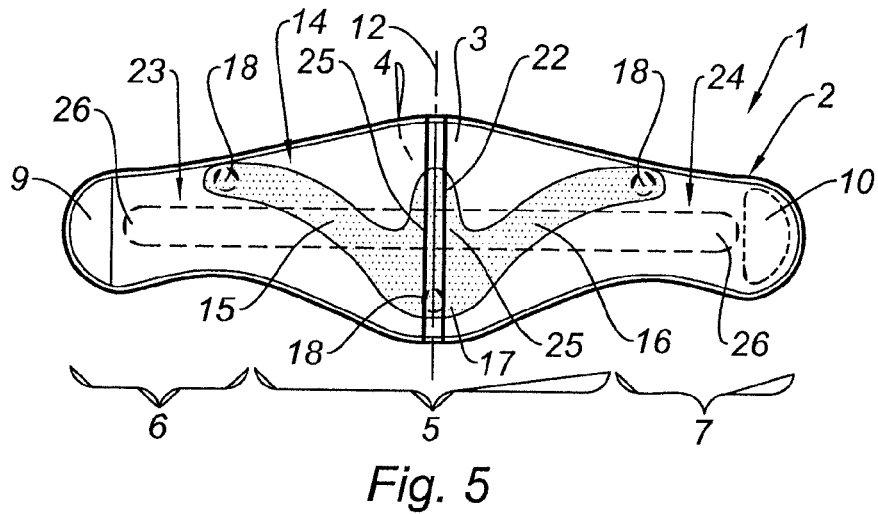
FIG. 5 is a planar view of the inner surface of a belt according to a second embodiment of the invention.
Figure 9:
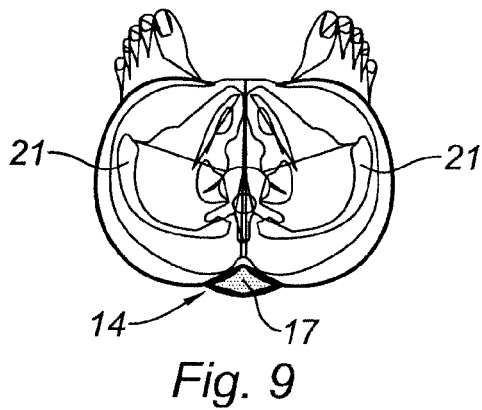
FIGS. 9 and 10 are diagrammatic views of a person wearing the belt of FIG. 5, in horizontal cross-section, respectively in a plane passing through the L4/L5 vertebrae (line I of FIGS. 6 to 8) and the L3 vertebra (line II of FIGS. 6 to 8).
Figure 10:
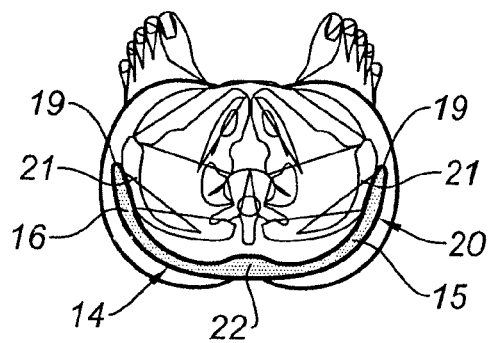

As diagrammatically illustrated in FIG. 5, the belt 1 can also comprise an additional tightening device which can in particular be used when the wearer must make a periodic effort. This device here comprises two additional lateral tightening straps 23, 24. Each strap 23, 24 comprises a first end 25 fastened on the outer surface 4 of the central portion 5 of the band 2. The second—free—end 26 of each strap 23, 24 comprises, on its inner surface, attachment means on the other strap and/or on the band 2.

As for the first embodiment, the cushion 14 is fastened to the band 2 removably and to that end comprises the three attachment areas 18 previously described. Thus, as illustrated in FIGS. 6 to 10, when the cushion 14 is fastened on the band 2 and the belt 1 is worn by a person in the appropriate position:

the free end portion 20 of each flange 15, 16 bears on the corresponding iliac crest 21 of the person;

the joining area 17 is in contact with the fifth lumbar vertebra (L5) and the top of the sacrum S (S1) of the person;

the appendage 22 is in contact with the persons' lumbar region, while fitting and at least partially filling in the lordosis;

the free end 19 of the flanges 15, 16 of the cushion 14 is located near each of the person's sides (see FIG. 8), i.e. in the illustrated embodiment, which is not limiting, the flanges 15, 16 do not extend to the lateral region of the person's abdomen.

Thus, the invention provides a decisive improvement to the prior art, by providing a belt whereof the effectiveness and wearing comfort are greatly improved.

Figure 6:
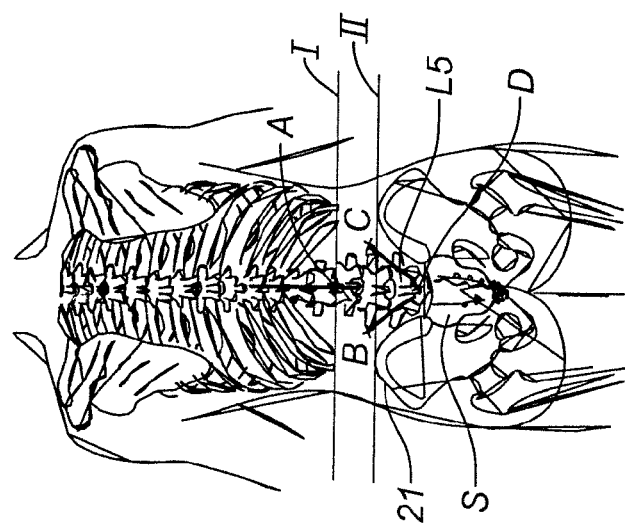
FIG. 6 shows a person from behind, without the belt.

The cushion 14, associated with the band 2, makes it possible to provide bearing and filling in for all or part of the Michaelis rhomboid, which is the seat of the most frequent lumbar pains. As shown in FIG. 6, this rhomboid is delimited by four points, i.e. the bottom of the lumbar groove A, the two sacro-illiac fossa B, C and the apex D of the gluteal fold.

The cushion 14 makes it possible to continuously maintain the antalgic pressure of the belt in the natural empty spaces: lumbar lordosis, bottom of lumbar groove and top of gluteal fold. The flanges of the cushion, which bear on the iliac crests, make it possible to increase the pressure in the soft area to improve the unloading of the lower vertebrae.

The invention is of course not limited to the embodiments described above as examples, but on the contrary encompasses all alternative embodiments.

The invention claimed is:

1. A lumbar support belt comprising:
    an elastic textile band positionable around a lower portion of a person's torso, said band having a transverse median axis and having a central portion that is widened relative to first and second end portions which, provided with complementary attachment means, are arranged to be placed on one another opposite the person's abdominal region and to be assembled by said attachment means; and
    a flexible cushion fastened on an inner surface of the central portion of the band, substantially centered relative to the transverse median axis of the band;
    wherein the flexible cushion includes two concave curved flanges defining a flared V shape, the two concave curved flanges having first end portions spaced apart from one another and second end portions joined at a joining area, wherein the joining area has a tip thereof that is oriented downward when the belt is worn, the cushion being designed and positioned so that, when the belt is worn, the first end portion of each flange bears on a corresponding iliac crest of the person and the joining area is in contact with an area comprising an upper portion of the sacrum and a fifth lumbar vertebra of the person.

2. The belt according to claim 1, wherein the cushion includes an appendage extending from the joining area upward, when the belt is worn, substantially along the transverse median axis of the band.

3. The belt according to claim 2, wherein, shown in cross-section in a plane orthogonal to the band and passing through the transverse median axis, the appendage has a domed shape arranged to at least partially fill in a lordosis of the person wearing the belt.

4. The belt according to claim 1, wherein the flanges of the cushion are curved toward an inside of the V.

5. The belt according to claim 1, wherein, when the belt is worn by a person, the first end portion of the flanges of the cushion are situated near each of the person's sides.

6. The belt according to claim 1, wherein, when the belt is worn by a person, the first end portion of the flanges of the cushion is situated in the lateral region of the person's abdomen.

7. The belt according to claim 1, wherein the cushion is removably attached to the band.

8. The belt according to claim 7, wherein the cushion comprises three attachment areas situated at the first end portion of the flanges and in the joining area, and an inner surface of the band comprises three additional localized attachment areas.

9. The belt according to claim 1, wherein the belt comprises at least one additional tightening strap.

* * * * *